United States Patent
Itai

(10) Patent No.: US 7,212,924 B1
(45) Date of Patent: May 1, 2007

(54) METHOD OF INFERRING THREE-DIMENSIONAL STRUCTURE OF PROTEIN

(76) Inventor: Akiko Itai, 5-16-6, Hongo, Bunkyo-ku, Tokyo (JP) 113-0033

( * ) Notice: Subject to any disclaimer, the term of this patent is extended or adjusted under 35 U.S.C. 154(b) by 0 days.

(21) Appl. No.: 09/508,527

(22) PCT Filed: Oct. 2, 1998

(86) PCT No.: PCT/JP98/04457

§ 371 (c)(1),
(2), (4) Date: Jul. 17, 2000

(87) PCT Pub. No.: WO99/18440

PCT Pub. Date: Apr. 15, 1999

(30) Foreign Application Priority Data

Oct. 2, 1997 (JP) .................................. 9-269611

(51) Int. Cl.
*G01N 33/48* (2006.01)

(52) U.S. Cl. ..................................................... 702/19
(58) Field of Classification Search .................... 435/6; 702/19, 27, 22; 530/300, 350
See application file for complete search history.

(56) References Cited

U.S. PATENT DOCUMENTS

| 5,241,470 | A | | 8/1993 | Lee et al. | |
| 5,436,850 | A | * | 7/1995 | Eisenberg et al. | 436/86 |
| 5,878,373 | A | * | 3/1999 | Cohen et al. | 702/22 |
| 5,948,763 | A | * | 9/1999 | Soto-Jara et al. | 514/14 |
| 6,512,981 | B1 | * | 1/2003 | Eisenberg et al. | 702/19 |

FOREIGN PATENT DOCUMENTS

| JP | 4-45781 | 2/1992 |
| JP | 5-282383 | 10/1993 |
| JP | 7-13959 | 1/1995 |
| JP | 7-93286 | 4/1995 |
| JP | 7-105179 | 4/1995 |
| JP | 7-206894 | 8/1995 |
| JP | 8-69446 | 3/1996 |
| JP | 10-95796 | 4/1998 |
| WO | 93/01484 | 1/1993 |

OTHER PUBLICATIONS

Bystroff et al., "Prediction of Local Structure in Proteins Using a Library of Sequence-Structure Motifs," Journal of Molecular Biology, 1998, vol. 281, pp. 565-577.*

Patent Abstracts of Japan for Publicatiuon No. 10095796.
Patent Abstracts of Japan for Publicatiuon No. 07206894.
Patent Abstracts of Japan for Publicatiuon No. 08069446.
Patent Abstracts of Japan for Publicatiuon No. 07105179.
Patent Abstracts of Japan for Publicatiuon No. 07093286.
Patent Abstracts of Japan for Publicatiuon No. 07013959.
Patent Abstracts of Japan for Publicatiuon No. 05282383.
Patent Abstracts of Japan for Publicatiuon No. 04045781.
Luthy et al., "Assessment of Protein Models with Three-Dimensional Profiles", *Nature*, vol. 356, pp. 83-85 (Mar. 5, 1992).
Chou et al., "Prediction of the Secondary Structure of Proteins from Their Amino Acid Sequence", *Adv. in Enzymology*, 47, pp. 45-148 (1978).
Branden et al., *Introduction to Protein Structure*, pp. 11, 12, 21, 22, and 249 (1992).
Branden et al., *Introduction to Protein Structure*, (1999), pp. 13-15, 24-25 and 349.
Martin, Yvonne C., Database accension No. 114:80616 CA XP002196005, abstract only.
Moon, J., and Howe, W., Proteins:, Struct., Funct., Genet. 11(4), pp. 314-328 (1991).
Boehm, Hans J., Database accenssion No. 119:66291 CA XP002196006, abstract only.
Boehm, Hans J., J. Computer-Aided Mol. Des. 6, pp. 61-78 (1992).
Satoru Kuhara et al., "A Deductive Database System PACADE for the Three Dimensional Structure of Protein", Proc. 24th Annual Hawaii International Conference on System Sciences, vol. 1, pp. 653-659 (1991).
John Spencer Evans et al., "Prediction of Polyelectrolyte Polypeptide Structures Using Monte Carlo Conformational Search Methods with Implicit Solvation Modeling", Protein Science, vol. 4, pp. 2019-2031 (1995).

* cited by examiner

*Primary Examiner*—Young J. Kim
(74) *Attorney, Agent, or Firm*—Greenblum & Bernstein, P.L.C.

(57) ABSTRACT

A method of predicting a scaffold of a protein comprising a query sequence, using a database which contains environmental information on the side chain of each amino acid residue contained in the amino acid sequence of each reference protein whose three-dimensional structure is known or predictable, and comprising: conducting matching based on the environmental information of each amino acid residue of each reference protein and hydrophobicity or hydrophilicity property of the side chain of each amino acid residue of the query sequence, choosing at least one template protein among the reference proteins that has high similarity in three-dimensional structure to the protein comprising the query sequence, and predicting the scaffold of the protein comprising a query sequence.

7 Claims, 1 Drawing Sheet

METHOD OF INFERRING THREE-DIMENSIONAL STRUCTURE OF PROTEIN

TECHNICAL FIELD

The present invention relates to a method for prediction of three-dimensional structures of proteins.

BACKGROUND ART

Prediction of three-dimensional structures of proteins from their amino acid sequences is not believed to be theoretically impossible. However, at present, any means to reliably predict the three-dimensional structures of proteins from sequence information has not been developed, and the means to know the three-dimensional structure of proteins are limited to experimental methods such as X-ray crystallographic analysis and NMR analysis. The information on the three-dimensional structure of proteins is essential for understanding their functions on atomic level, as well as for designing medicinal molecules targeting that protein or useful proteins with excellent functions. Recently, as the result of rapid progresses of analytical means of genetic information, numbers of proteins are increasing whose sequence information are elucidated without isolation. Therefore, development of effective means to predict three-dimensional structure and functions from sequence information is desired earnestly at present.

When the existence of a protein with a certain amino acid sequence is revealed, it is a common practice to search for proteins with homology from sequence databases. In case a protein having reasonable degree of identity in amino acid sequence is found, alignments are performed by considering homology and gaps with the protein, and alignments of higher homology are further searched. It can be assumed that when the homology of the sequence of the target protein with a protein with known function is high, its function resembles that of the known protein, and when the homology of the target protein with a protein of a known three-dimensional structure is high, its three-dimensional structure resembles that of the known protein. As the homology is higher, the possibility of the resemblance in functions or three-dimensional structure is also higher, and the reliability of predictions is believed to be high.

When the homology to the protein sequence with known three-dimensional structure is recognized to a certain extent (generally about 30%) or more, homology modeling methods are performed to construct a three-dimensional structure using the three-dimensional structure as a template. When the residues differ from those corresponded in the template in view of its three-dimensional structure, the three-dimensional structure can be constructed virtually by substituting side chains. Gaps in the alignment need to be treated separately because no corresponding amino acid residues exists in the template three-dimensional structure or the template has excess amino acid residues. Since the existence of gaps makes the template-based modeling difficult, and since it also lowers reliability, alignment methods giving some penalty to the gaps are recommended in order to reduce the number of gaps as small as possible.

When any protein with known three-dimensional structure is not found which has a fairly high sequence homology with the amino acid sequence in question, homology modeling is impossible. On the other hand, as the crystal structure information on proteins is accumulated, there have been revealed by a lot of researches that plural proteins with little homology and completely different functions to each other have similar three-dimensional structures. This fact indicates a possibility that a three-dimensional structure fitting as a template can be chosen from proteins with known three-dimensional structures, even though homology of amino acid sequence is low, by consideration of physicochemical factors for proteins to form stable three-dimensional structures.

Recently, by using scores considering the coincidence of physical properties such as hydrophobicity for each amino acid residue, methods have been developed for choosing template proteins from proteins with known three-dimensional structures, which template proteins have high similarity in three-dimensional structure even though they have low homology in amino acid sequence. A typical method includes the 3D-1D method (R. Luthy, J. U. Bowie and D. Eisenberg, Nature, 356, 83, 1992) by Eisenberg et al. This method, in addition to the consideration of homology of amino acid sequences, contains the calculating process of similarity scores between the corresponded amino acid residues using parameters expressing the secondary structure to which each amino acid residue belongs, and the environment of the location of the residues in proteins with known three-dimensional structure, together with parameters given to each amino acid residue in each secondary structure in the query sequence. This method can avoid the problem of huge degrees of freedom in folding peptide chains of proteins by utilizing the known crystal structures as the template, and thus a modeling is enabled by including the physical parameter such as hydrophobicity as a factor of estimation even when the homology in sequence is low.

However, even in case the three-dimensional structure is similar, since there are few proteins in which the number of amino acid residues, a secondary structure, or the lengths of or loops are the same, a lot of problems will arise when the 3D-1D method are practically applied based on the correspondence between the amino acid sequences. For example, although it is necessary to correspond amino acid residues by considering the deletion of partial sequences (gaps) in either sequence, as well as the simple slide between the amino acid sequences (threading), the introduction of gaps reduces the reliability as similarly observed in the homology-modeling. When the homology in sequence is low, how to make the correspondence of the sequences with consideration of the necessary and minimum gap is a problem. Furthermore, in the aforementioned method, no advancement of predictability is expected by improving parameters because it depends on numerous parameters such as hydrophobicity and hydrophilicity, as well as parameters given for each of twenty amino acid residue in each secondary structure.

The history of study to predict the three-dimensional structure of proteins from amino acid sequences started with the prediction of which fragment of the sequence would be in what secondary structure. That is, by employing parameters which shows the susceptibility of adopting α-helix or β-sheet for each amino acid residue or each set of several amino acid residues, obtained statistically from crystallographic information a lot of proteins, the continuous region is detected which shows remarkable tendency from the query amino acid sequence, and the secondary structure is chosen for each region. A typical example include a secondary structure prediction method by Chou and Fasman (P. Y. Chou, & G. D. Fasman, Adv. Enzymol. 47, 45, 1978). However, this sort of method gives no information about three dimensional assemblies of secondary structures, and since the average coincidence between secondary structures predicted from amino acid sequences and those found in crystal structures is approximately 60%, it has almost no value as a prediction method of three-dimensional structures.

Methods of predicting stable folding structures of proteins by pure calculation without preconception (so-called ab initio prediction method) have been attempted. However, since proteins are molecules with extremely huge degrees of freedom (even for the protein with about 100 residues, the number of parameters to be considered for the degrees of freedom is more than 400), it is impossible to search possible structures sufficiently considering all degrees of freedom by means of presently available computers. Moreover, from the reasons that studies for the factors related to the stabilization of protein structure (for example, physicochemical properties of water, hydrophobic interaction, electrostatic interaction) are not advanced enough to estimate the stability of possible three-dimensional structures correctly, success of this kind of structure prediction is not expected at present.

In recent years, three-dimensional structures of a lot of proteins have been analyzed, and the results are available from Protein Data Bank. At present, structures of about 6,000 proteins and nucleic acids are stored, however, independent proteins with different functions are approximately 400. From the three-dimensional structures of these proteins, many proteins have been revealed to have the same structural motif, although they have no homology and seem to have no relation evolutionally and functionally to each other.

DISCLOSURE OF THE INVENTION

The first object of the present invention is to provide a method of modeling a three-dimensional structures of a protein with a given amino acid sequence by the prediction of a scaffold likely possessed by the protein based on the information of the amino acid sequence of the protein. Prediction of a correct scaffold can be the cornerstone of the modeling of a three-dimensional structure with desired precision. An ultimate object of the present invention is to provide a method of predicting the three-dimensional structure of a protein solely based on an amino acid sequence information. For that purpose, a specified object of the present invention is to provide a method of predicting a scaffold. Another object of the present invention is to provide a useful database for the above-mentioned method.

The inventors conducted zealous researches to achieve the foregoing objects. As a result, by preparing a database which contains environmental information on the side chain of each amino acid residue of proteins whose three-dimensional structures are known or predictable, and by using the database, the inventors found a method for predicting a scaffold possibly possessed by a protein, with high reliability and efficiency, based on the amino acid sequence information of the protein with unknown three-dimensional structure.

The present invention thus provides a method of predicting a scaffold of a protein comprising a query sequence, wherein said method uses a database which contains environmental information on the side chain of each amino acid residue contained in the amino acid sequence of each reference protein whose three-dimensional structure is known or predictable, and wherein said method comprises the step of:

conducting matching based on the environmental information on each amino acid residue of each reference protein and hydrophobicity or hydrophilicity property of the side chain of each amino acid residue of the query sequence, and choosing at least one template protein among the reference proteins that has high similarity in three-dimensional structure to the protein comprising the query sequence.

After the prediction of the scaffold, a three-dimensional structure (three-dimensional atomic coordinates) corresponding to the query sequence is obtained based on the optimum matching between the template protein and the query sequence.

According to preferred embodiments of the present invention, there are provided:

the aforementioned method wherein the amino acid sequence of each of the reference proteins is divided into two or more segment sequences comprising two or more continuous amino acid residues based on the three-dimensional structure of the reference protein;

the aforementioned method wherein the amino acid sequence of each of the reference proteins is divided into one or more core segment sequences, which substantially participate in the formation of hydrophobic core, and into one or more sub segment sequences which do not substantially participate in the formation of hydrophobic core;

the aforementioned method wherein the matching is conducted based on the information on the degree of burial into the inside of the protein or the degree of exposure to the protein surface of the side chain of each amino acid residue in the reference protein, as well as the properties of hydrophobicity or hydrophilicity of each amino acid residue in the query sequence;

the aforementioned method wherein the matching is performed by sliding one or more core segment sequences of the reference protein on the query sequence without consideration of any gaps except those at one end or both ends of the core segment sequences; and the aforementioned method wherein the gap is a deletion or addition of one or more amino acid residues.

According to further preferred embodiments of the present invention, there are provided: the aforementioned method wherein the matching comprises the following steps:

(a) the step of matching by sliding one or more core segment sequences on the query sequence, optionally considering any gaps at one end or both ends of the core segment sequences, provided when two or more core segment sequences are used, the core segment sequences are placed in the order of appearance on the amino acid sequence of the reference protein; and (b) for a part of the query sequence which is not subjected to the matching to the core segment sequence in process (a), the step of sliding one or more sub segment sequences on the query sequence, optionally considering any gaps, according to the linkage of each of the core segment sequence in the reference sequence.

The invention also provides the aforementioned method in which the optimum matching is selected based on calculated scores obtained from the environmental information on the side chains of the amino acid residues of the reference protein and the hydrophobicity parameters of the corresponding amino acid residues on the query sequence; and the aforementioned method which comprises the step of normalizing the above scores by using a self matching score for the reference protein.

From another aspect, the present invention provides a database which contains environmental information on the side chains of amino acid residues of one or more reference proteins with known or predictable three-dimensional structures, and which is used for the above mentioned methods.

This database is stored and distributed in usual media for instance, magnetic disks, photonic disks, CD-ROMs, magnetic tapes and the like, and is usable to predict a stable scaffold of a protein comprising the query sequence by matching utilizing scores that reflect the coincidence between the environmental information and the properties of amino acid residues of the query sequence.

BEST MODE FOR CARRYING OUT THE INVENTION

The methods of present invention are characterized by selecting at least one template protein which is stereo-structurally similar to the protein comprising the query sequences from a database containing reference proteins, and then predicting the three-dimensional structure of the protein comprising the query sequence based on the template protein scaffolds, instead of searching and estimating all theoretically possible folding of main chains from the query sequence. The methods of the present invention are carried out rapidly by using commonly used computers such as workstations, personal computers and the like.

The terms used in the specification should be interpreted in the broadest sense including the concept mentioned below.

"Three-dimensional structure" means the structure of a protein expressed in three-dimensional atomic coordinates. In some cases atomic coordinates of all existing atoms including those in side chain in each residue are available, and in other cases part of them are omitted. "Modeling" means the construction of the three-dimensional structures which has high possibility of existence for a given protein and the presentation of the result in three-dimensional atomic coordinates, regardless of whether or not the three-dimensional structure is experimentally elucidated.

Figure 1:
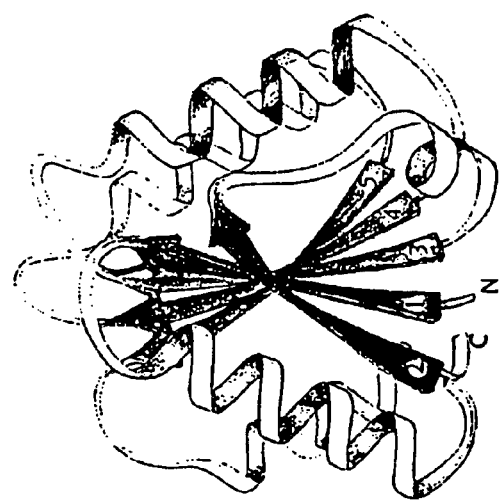
FIG. 1 shows the relationship among "three-dimensional structure", "structure motif" and "scaffold". In the FIGURE, (a) shows the three-dimensional structure, (b) shows the structure motif, and (c) shows the scaffold.
Figure 1:
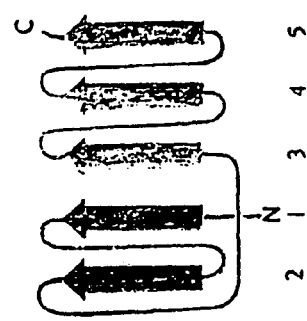
Figure 1:
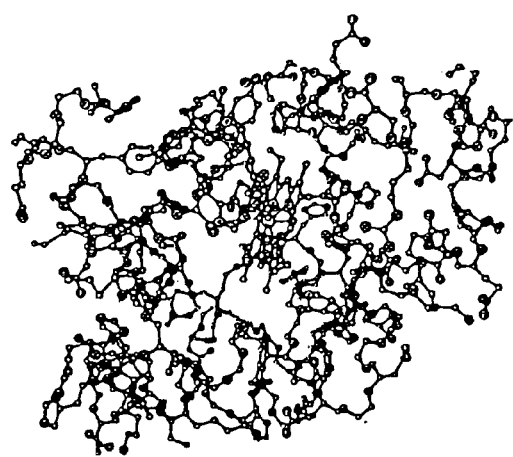

Terms such as "secondary structure", "structure motif" and "scaffold" are described in the article by Branden and Tooze (Carl Branden and John Tooze, Introduction to Protein Structure, Garland Publishing Inc. New York, 1991: Japanese translation "Introduction to Protein Structure", Kyoikusha, 1992). "Structure motif" and "scaffold" are common in expressing the topology of only peptide main chains. However, "structure motif" expresses the combination of secondary structure groups and peptide chain linkage schematically and two-dimensionally, whist "scaffold" means the frame of three-dimensional structure of proteins including the assembly of secondary structure groups. The relationship among "three-dimensional structure", "structure motif," and "scaffold" is shown in FIG. 1.

Amino acid sequence whose three-dimensional structure is desired to be predicted is called a "query sequence", and the protein having the query sequence is called a "protein comprising the query sequence". A protein whose three-dimensional structure is known or predictable or that included in the databases of the present invention is called a "reference protein". Among the reference proteins, those proteins which have good matching scores with the query sequence and are selected as high similarity proteins in three-dimensional structure with the protein comprising the query sequence are called "template proteins" (or may also be referred to as "template candidate proteins"). The scaffold of the template protein is used as a template when the three-dimensional structure of the protein comprising the query sequence is constructed.

Generally, the operation or result of parallel corresponded arrangement of two or more sequences so as to obtain a high degree of identity and homology is called "alignment" ("identity" means the strict coincidence of corresponding residues between the sequences, and "homology" means a certain degrees of coincidence that allows ambiguity such as nearly identical or similar to.). In the methods of the present invention, "matching" (or "correspondence") means operation or result of parallel arrangement of corresponded residues based on the coincidence of environment information and properties, regardless of the identity or homology of amino acid residues. The degree of identity in a correspondence between the environmental information of each amino acid residue in the reference protein and the properties of amino acid residue in the query sequence is called "matching score" (or simply "score"). "Environmental information" means mainly the degree of exposure to the protein surface and the environment of the side chain group of each amino acid residue in the three-dimensional structure of the reference protein. The term "gap" used herein means the lack of one or more corresponding amino acid residues in any one of sequences included in the correspondence of two or more amino acid sequences. Based on one sequence, the term means insertion or deletion of one or more amino acid residues.

According to preferred embodiment of the present invention, information on two or more segment sequences divided so as to reflect the three-dimensional structure of each of the reference proteins and environmental information on each amino acid residue are stored in the aforementioned database. Matching of two sequences are conducted based on matching scores calculated from environmental information of a reference protein and hydrophobicity parameters of corresponding amino acid residues of a query sequence. It is desirable that numerical values are assigned beforehand to 20 kinds of amino acid residues as the hydrophobicity parameter.

Among segment sequences, core segment sequences which participate in the formation of hydrophobic core are slid on the query sequence without any gaps to carry out matching with consideration of the addition or reduction of amino acid residues only at the both ends of the segments (take one or more amino acid residues from the end of neighboring sub segment sequence and insert them into the core segment sequence, or the reverse procedure is conducted) to select template candidate proteins with good scores. Then, for the sub segment sequences which do not participate in the stabilization of hydrophobic core, matching is carried out by optionally considering any gaps to reduce the number of template candidates. Final selection of at least one template protein is conducted by comparing the optimized matching score of each protein with a normalized self matching score.

The methods of the present invention are based on the assumption that a higher matching score reflects a higher similarity of scaffold and three-dimensional structure between two sequences, and the method is characterized in that it enables an appropriate selection of at least one template protein from the reference proteins by performing matching of residues between sequences even with little homology based on the folding principle of proteins. According to the preferred embodiment of the present invention, the method include as key steps (1) preparation of a database; (2) matching using one or more segment sequences; (3) calculation of matching scores; (4) selection of template candidate proteins from reference proteins; and (5) selection of at least one template protein.

invention will be explained more specifically with reference to the scheme. However, the method of the present invention is not limited to the details of the scheme or the details of the following explanations.

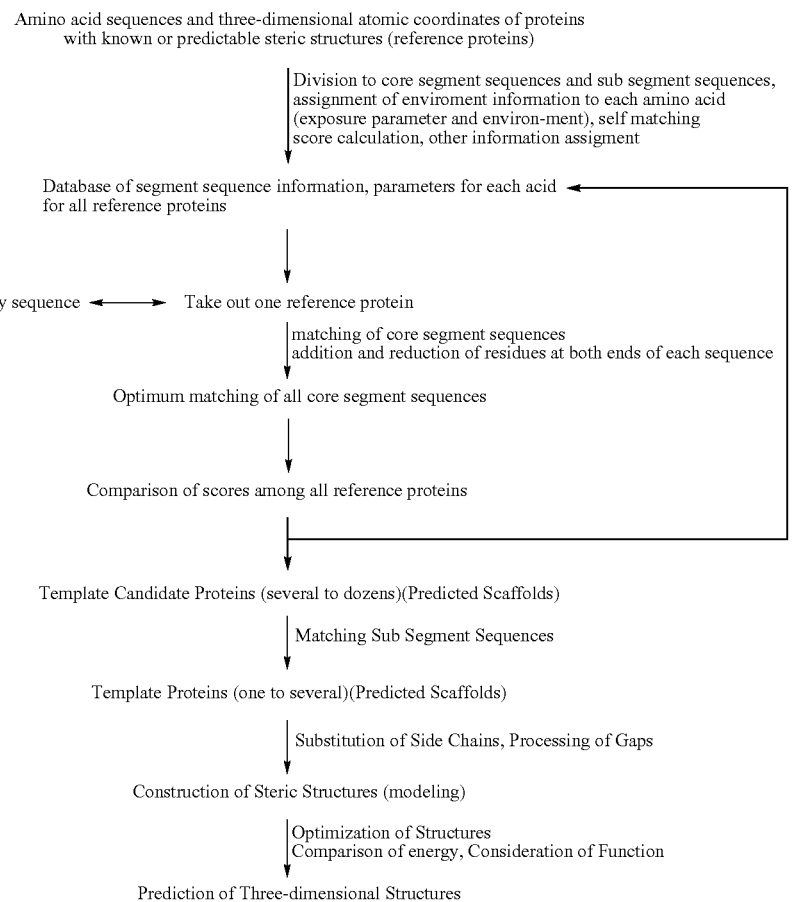

In peptide chains of water soluble single subunit proteins, in general, it is advantageous from the viewpoint of free energy that hydrophobic side chains of amino acid residues are buried as much as possible inside of molecules so as not to be exposed, whilst hydrophilic side chains expose on the protein molecule surface as much as possible. However, in case of proteins existing in different environment such as those interacting with cell membrane or those composed of multiple subunits, hydrophobic side chains may sometimes expose on the protein surface when individual protein structure or subunit structure is solely considered. The methods of the present invention consider these variety of three-dimensional structures of proteins, it enables to give scores reflecting the environment of each amino acid residue. The concept of susceptibility of specific secondary structure for each amino acid residue (for example, P. Y. Chou & G. D. Fasman, Adv. Enzymol. 47, 45, 1978) is not used basically, but it is possible to employ scores including those concepts if desired.

EXAMPLE

A preferred embodiment of the present invention is shown in the following scheme, and the methods of the present (A) Preparation of Database For the reference proteins whose three-dimensional structures are known or predictable, as information related to the three-dimensional structures, a database is prepared which contains environmental information on each amino acid residue and information on segment sequences. Any protein can be stored in the database as an entry as long as the information on three-dimensional structure of the protein is known or predictable. At the same time, when plural subunits are included in the protein whose structure is determined, it is preferable to treat each of the subunits as an independent entry. As regards a structure comprising plural domains linked by one or more peptide chains, it is preferable to treat each domain as an independent entry together with the whole structure.

Information to be included for each reference protein is as follows:

(1) General Information (a) In formation of the name of protein (protein code), subtype, number of amino acid, amino acid sequence, domain, subunit;

(b) As information concerning the three-dimensional structure, appropriate information may be included such as the determination (or prediction) method of three-dimensional structure (by which of crystal analysis, NMR, or modeling the three-dimensional structure is determined), PDB code, name of a protein used as a template in case of modeling, and chemical name of co-crystalized molecules when available in case of crystal analysis; and (c) As information concerning the biological significance, information may be included such as biological function, species, existing tissues and organs, and effecter molecule.

(2) Segment Sequence Information

Based on characteristics in the three-dimensional structure of a protein, the sequence is divided into two or more segment sequences, and it is desirable to include the following information in the database for each segment sequence.

(a) Serial number of the segment sequence from the N-terminal;

(b) Flag indicating whether the segment is a core segment sequence or a sub segment sequence;

(c) The beginning and the end (serial number of the amino acid of the sequence from the N-terminal), length of the sequence, the distance and vector, smallest number of residues if the sequence is a sub segment sequence;

(d) Distance and vector between segment sequences;

(e) Segment sequence number of a partner sequence which forms one or more hydrogen bonds to allow the formation of β-sheet, and the distinction between antiparallel or parallel β-sheet, or segment sequence number located within a given distance;

(f) Self matching score (explained later)

Criteria of division to segment sequences are not particularly limited. It is possible to regard certain segment sequences as core segment sequences which form secondary structures such as α-helix structure and β-strand structure and substantially participate in the formation of a hydrophobic core, and other segments as sub segment sequences. It is desirable that each segment sequence comprises, for example, a continuous sequence including 7 or more residues. As regards β-turn structure, it may be added to the core or the sub segment sequence at the beginning, or alternatively, the structure may be distinguished with other flag and determined later at the time of search whether it employs as the core or the sub segment sequence. Procedure for the division may be conducted on the computer graphics interactively for each protein, or may be done automatically by providing programs with defined criteria of division. As the judging criteria, for example, numerical values such as pseudo torsion angle formed by adjacent four C-alpha atoms may be used so as to enable automatic division of segment sequences.

(3) Environmental Information on Each Amino Acid Residue (a) Exposure Parameter

For all reference proteins, the degree of exposure of side chains to the protein surface and the degree of burial of side chains into the inside of the protein are calculated for each residue based on the three-dimensional structures, and then exposure parameters are assigned based on the calculated values. The term "exposure parameter" used herein means the numerical values indicating what degree of the side chain of each residue is exposed on the molecular surface or buried. Methods of defining exposure parameter are not particularly limited, and any methods may be employed. It is desirable to assign negative values for those having a high degree of exposure and positive values for those having a low degree of exposure. For example, it is possible to calculate the surface area that permits contact with a solvent and that contacts the protein atoms for each amino acid side chain in the three-dimensional structures, and usable exposure parameter can be calculated based on the difference of the areas. It is also possible to determine the parameter using as a criterion the ratio of solvent contacting surface based on the whole molecular surface.

(b) Set Up of Environment Flag

In proteins which interact with cell membranes, side chains of hydrophobic amino acid residues are exposed to the surface region that interacts with membranes, and in proteins which have contacting surface regions stabilized by the assembly of subunits or domain structures, the side chains of hydrophobic amino acid residues are sometimes exposed to the contacting surface regions. These proteins have different properties from water soluble proteins that exist individually. For these proteins, the folding principle described above, per se, may not be applied generally. When the database is prepared, for example, it is possible to give the following environment flag to each amino acid residue separately from the exposure parameter.

For example, from the origin of the protein or experimental results concerning function and the three-dimensional structures thereof, it is possible to estimate to which of the following categories the existing environment of side chain of each amino acid residue belongs, and to assign an environment flag so as to be taken into account at the time of matching and calculation of scores.

0: unknown (undefined or indefinable)

1: intramolecular contact (contact with the inside of protein, subunit, and domain)

2 molecular cavity (ligand-binding sites)

3: molecular surface (contact with water environment

4: molecular surface (contact with other protein, other subunit, and other domain)

5: molecular surface (contact with membrane)

In addition, for amino acid residues which give special effects on the formation of three-dimensional structures, flags are provided to indicate as special residues so as to be taken into account at the time of matching and score calculation. For example, the flag may be applied to S—S bonded cysteine residues, amino acid residues without a hydrogen bonding functional group in the main chain such as proline, or residues which are capable of forming strong hydrophilic interactions between side chain atoms.

(B) Matching Between the Sequences of the Query Sequence and the Reference Protein In order to search for optimum matching efficiently by sliding one sequence on the other sequence, it is possible to employ the concept of segment sequences. For that purpose, the above-mentioned database stored segment sequence information obtained from the three-dimensional structure of each reference protein and environment information on each amino acid residue in the order of amino acid sequence. On the other hand, information possessed by the query sequence is solely the information about the amino acid sequence, and accordingly, values taken from the table of hydrophobicity parameter are applied to each amino acid residue for calculation of scores. Choosing a reference protein one by one from the database and sliding segment sequences on the query sequence, which are placed in the order of appearance in the amino acid sequence, and then a matching is searched that gives the best matching score between the segment sequence groups and the query sequence.

(1) Matching Utilizing Segment Sequences

By utilizing segment sequences, and also by conducting matching of amino acid residue as an unit for the core segment sequences without consideration of any gaps, it is possible to search for correspondence between sequences that allows rapid optimum matching. Generally, in the process of evolution, insertion and deletion of residues as well as substitution generally occur, and consideration of which is essential for the matching of sequence (see, Background Art). However, in most cases gaps exist in sub segment sequences. This is because if insertion or deletion takes place other than at the both ends of the core segment sequences which participate in the stabilization of hydrophobic core, the stable scaffold, per se, is destroyed and the three-dimensional structure of the protein is drastically changed.

Therefore, according to preferred embodiment of the present invention, the matching is carried out in two steps by separating core segment sequences and sub segment sequences. In the first step of matching using the core segment sequences, one or more core segment sequences are slid on the query sequence without consideration of any gaps to carry out matching for searching the optimum matching with consideration of an increase or decrease of amino acid residues only at the both ends of each core segment sequence.

Matching score is calculated and stored while each core segment sequence is slid on the query sequence. After calculation is completed for all the core segment sequences in the same manner, the optimum matching as a whole is determined. When two or more core segment sequences are used, two or more core segment sequences are placed on the query sequence in the order of appearance in the amino acid sequence of the reference protein so as to avoid any overlap, and under the assumption that the existence of four or more amino acid residues is necessary between the core segment sequences (the number of amino acid residues required for linkage of two adjacent core segment sequence in order, e.g., β-turn, within sterically bondable number of amino acid residues), the core segment sequences are slid on the query sequence without changing the order to chose the matching with the best total score. It is not necessary that the matching score of each core segment sequence is maximum. In this first step, several to dozens template proteins which give high scores are chosen as candidates for scaffold to proceed the second step.

(c) Matching Score

Matching scores are calculated using exposure parameter EP(i) of environment information from the reference protein and hydrophobicity parameter HB (j) from the query sequence for each residue. The symbol "i" indicates the serial amino acid residue number in the amino acid sequence of the reference protein, and the symbol "j" designates the residue number of the query sequence corresponded thereto. Any equation can be used for the calculation of the matching score so far that it gives a high score when strongly hydrophobic amino acid residues of the query sequence correspond to the side chain environment buried inside of the reference protein molecule, and when strongly hydrophilic amino acid residues of the query sequence correspond to the side chain environment exposed to the molecular surface. Most simply, for example, the matching score may be calculated by the following equation.

Matching score for each residue=$EP(i) \times HB(j)$

Matching score of each segment sequence=sum of matching scores of residues contained in the sequence Matching score of the whole sequence=sum of matching scores of all segment sequences (1) Hydrophobicity Parameter To each of 20 kinds of amino acid residues, hydrophobicity parameter related to the properties of hydrophobicity or hydrophilicity is provided. A method of determination of hydrophobicity parameter is not particularly limited, and any value based on any criterion may be used. For example, hydrophobicity value for each amino acid listed on the literature may be used, or alternatively, those calculated by an appropriate method based on in house criteria may be used. For example, for a certain amino acid residue, the ratio of residue buried inside a protein molecule is statistically obtained in view of the total appearance of the residue in all the proteins crystallographically analyzed, and then the ratio may be used as the hydrophobicity parameter of the amino acid residue.

Furthermore, for example, different values may be given to different amino acid residue, or alternatively, hydrophobicity parameters graded as shown in the following table may be assigned.

TABLE 1

| | |
|---|---|
| 2 | Strong hydrophobicity (isoleucine, valine, leucine, phenylalanine) |
| 1 | Weak hydrophobicity (alanine, methionine, cystine, tyrosine) |
| 0 | Almost neutral (glycine, proline, lysine, arginine) |
| −1 | Weak hydrophilicity (threonine, histidine) |
| −2 | Strong hydrophilicity (serine, asparagine, aspartic acid, glutamine, glutamic acid) |

(2) Self Matching Score

In order to compare the degree of matching to the query sequence among the proteins with different number of amino acid residues and different composition of amino acid residues, it is desirable to normalize the scores. For that purpose, for each reference protein, matching score is calculated beforehand from the exposure parameters EP(i) of the amino acid sequence of the reference protein and hydrophobicity parameters HB(i) of the environment information stored in the database, and then the matching score is stored in the database. For example, the calculation may preferably be carried out by using the following equation.

Self matching score=$\Sigma(EP(i) \times HB(i))$

After the matching of all segment sequences to the query sequence is completed and the optimum matching is obtained, normalization may be carried out by multiplying the resulting matching scores by the self matching scores. By comparing normalized optimum matching scores among all reference proteins, an optimum template candidate protein can be selected. The self matching score and the matching score tend to be larger values as the number of amino acid residue becomes larger.

(D) Selection of a Template Candidate Protein

A process of choosing at least one template candidate protein may approximately comprises the following steps of:

(a) taking out reference proteins one by one from the database, and conducting the matching using the query sequence;

(b) calculating matching scores for core segment sequences by sliding the sequences on the query sequence without consideration of any gaps;

(c) carrying out the matching to obtain an optimum matching optionally by increasing or decreasing residues at N-terminal or C-terminal of each core segment sequence;

(d) for all reference proteins, carrying out the steps (a) through (c) to obtain optimum matchings and matching scores;

(e) choosing template candidate proteins from the reference proteins with good scores based on the normalized scores (in this step, those structures can be candidates for scaffolds of the query sequence);

(f) carrying out the matching of sub segment sequences that link core segment sequences, and obtaining the optimum matching and matching score by considering a difference in length of the sequences of the query sequence from the corresponding segment sequence and the existence of any gaps; and (g) choosing at least one template protein based on the normalized score.

(E) Construction of Three-Dimensional Structures

The three-dimensional structure of the protein comprising the query sequence can be constructed by substituting side chains of amino acid residues based on the structure of the scaffold of the template protein and the results of the optimum matching between the reference protein and the query sequence, and three-dimensional atomic coordinates corresponding to the query sequence can be obtained. When two or more template proteins are chosen which are difficult to be discriminated, it is desirable to construct three-dimensional structures for all of them. When the length of a sub segment sequence is different from that of the template candidate, databases and the like may be used, which contain loop structures appeared in crystal structures, so as to be able to determine an appropriate topology of the sub segment sequence. For segments where the scaffold of the template is modified, its topology can be determined by considering the properties of residues and the degree of exposure in the same manner as the matching scores. After the thorough examination for the presence of serious steric hindrance or vacant space inside the molecule that unstabilizes the three-dimensional structure, and after fine adjustment of the structure by calculations for structural optimization and molecular dynamics, the stability of three-dimensional structures are compared.

In the final step, three-dimensional structures constructed based on all templates are ranked based on energies and matching scores. When functions of the protein comprising the query sequence are known, information such as correspondences to the known functions of the template proteins, the adequacy of the position of amino acid residues assumed to be involved in the appearance of the functions in the three-dimensional structure, and influences on the functions by amino acid mutation can be utilized for the selection of the template protein.

INDUSTRIAL APPLICABILITY

According to the methods of the present invention, it is possible to reliably and efficiently obtain information concerning the three-dimensional structure of a protein comprising essentially of an amino acid sequences, solely from the information of the amino acid sequence, based on an amino acid sequence database of proteins whose three-dimensional structures are known or predictable.

What is claimed is:

1. A method of predicting a scaffold of a protein comprising a query sequence, wherein said method uses a database which contains environmental information on the side chain of each amino acid residue contained in the amino acid sequence of each reference protein whose three-dimensional structure is known or predictable, wherein the amino acid sequence of each of the reference proteins is divided into two or more core segment sequences comprising two or more contiguous amino acid residues based on the characteristics of the three-dimensional structure of the reference protein, wherein the amino acid sequence of each of the reference proteins is divided into two or more core segment sequences which are predetermined to form a hydrophobic core, and into one or more sub segment sequences which are not predetermined to form a hydrophobic core, and wherein said method comprises:

conducting matching based on the environmental information on each amino acid residue of each of the two or more core segment sequences of the reference protein and hydrophobicity or hydrophilicity property of the side chain of each amino acid residue of the query sequence, and wherein the matching is performed by sliding the two or more core segment sequences of the reference protein on the query sequence without consideration of any gaps except those at one end or both ends of the core segment sequence, and choosing at least one template protein among the reference proteins that has highest similarity in three-dimensional structure to the protein comprising the query sequence based on the matching score of the whole sequence and predicting the scaffold of the protein comprising a query sequence.

2. The method according to claim 1, wherein the matching is conducted based on the information on degree of burial into the inside of the protein of the side chain of each amino acid residue in the reference protein, or degree of exposure to the protein surface of the side chain of each amino acid residue in the reference protein, together with the properties of hydrophobicity or hydrophilicity of each amino acid residue in the query sequence.

3. The method according to claim 1, wherein the gap is a deletion or addition of one or more amino acid residues.

4. The method according to claim 1, wherein the matching comprises: matching by sliding the two or more core segment sequences of the reference protein on the query sequence, optionally considering gaps at one end or both ends of the core segment sequences, wherein the core segment sequences are placed in the order of appearance on the amino acid sequence of the reference protein; and, sliding one or more sub segment sequences on the query sequence, optionally considering one or more gaps.

5. The method according to claim 1, wherein an optimum matching is selected based on calculated scores obtained from the environmental information on the side chains of the amino acid residues of the reference protein and the hydrophobicity parameters of the corresponding amino acid residues on the query sequence.

6. The method according to claim 5, which further comprises normalizing said calculated scores by using a self matching score for the reference protein.

7. The method according to claim 1, which further comprises constructing the three-dimensional structure of the protein comprising the query sequence.

* * * * *